(12) United States Patent
Seltzer et al.

(10) Patent No.: US 6,327,889 B1
(45) Date of Patent: Dec. 11, 2001

(54) DEVICE AND METHOD FOR INTRODUCING SURROGATES, PARTICULARLY METAL SURROGATES, INTO AN EXHAUST STREAM, FOR SIMULATING AN EXHAUST STREAM, AND FOR ESTABLISHING A STANDARDIZED SOURCE

(75) Inventors: Michael D. Seltzer, Ridgecrest, CA (US); Gerhard A. Meyer, Worthington, OH (US)

(73) Assignee: The United States of America as represented by the Secretary of the Navy, Washington, DC (US)

(*) Notice: Subject to any disclaimer, the term of this patent is extended or adjusted under 35 U.S.C. 154(b) by 0 days.

(21) Appl. No.: 09/467,849

(22) Filed: Dec. 20, 1999

(51) Int. Cl.[7] ........................... G01J 3/443; G01N 21/73; G01N 1/00; G12B 13/00
(52) U.S. Cl. ................................ 73/1.02; 73/1.03; 436/9; 356/316; 356/243.2
(58) Field of Search .................................... 73/1.03, 1.05, 73/1.2, 1.02–1.71, 1.23; 436/9; 356/316, 36, 243

(56) References Cited

U.S. PATENT DOCUMENTS

| | | | |
|---|---|---|---|
| 4,660,408 | * 4/1987 | Lewis | ........................................ 73/28 |
| 5,596,405 | 1/1997 | Seltzer et al. | .. |
| 5,918,254 | * 6/1999 | Bottiger et al. | ........................ 73/1.06 |
| 6,044,688 | * 4/2000 | Dilger | .................................... 73/1.05 |

* cited by examiner

Primary Examiner—Hezron Williams
Assistant Examiner—David J. Wiggins
(74) Attorney, Agent, or Firm—Earl H. Baugher, Jr.; Anthony J. Serventi

(57) ABSTRACT

A convenient apparatus and method for inserting surrogate metal-entraining aerosols into exhaust stacks for the purpose of realistic dynamic testing of an emissions monitor. The aerosols contain elements required to be detected by the monitor. The 14 metals regulated by the EPA as hazardous air pollutants are of particular interest. The method requires less time and fewer skilled technicians than conventional testing methods. In a preferred embodiment of the present invention, a burner (e.g., propane or kerosene) is combined with a combustion chamber, a fan, an air compressor, at least one peristaltic pump, at least one surrogate reservoir, and the necessary ductwork for connection to an exhaust stack. The amount of surrogate aerosol to be introduced to the stack is adjusted at the peristaltic pump. After heating by the burner and subsequent introduction into the hot stack, the surrogate homogeneously mixes with the exhaust stream and is presented to the sensor as a dry gas component of the exhaust stream. Other applications include use as an exhaust stack simulator and as a standardized source of aerosols containing hazardous air pollutants, in particular metal-entraining aerosols.

24 Claims, 3 Drawing Sheets

DEVICE AND METHOD FOR INTRODUCING SURROGATES, PARTICULARLY METAL SURROGATES, INTO AN EXHAUST STREAM, FOR SIMULATING AN EXHAUST STREAM, AND FOR ESTABLISHING A STANDARDIZED SOURCE

STATEMENT REGARDING FEDERALLY SPONSORED RESEARCH OR DEVELOPMENT

The invention described herein may be manufactured and used by or for the government of the United States of America for governmental purposes without the payment of any royalties thereon or therefor.

FIELD OF THE INVENTION

The present invention pertains to an aid for performance testing a sensor. In particular, a preferred embodiment is a dry-gas-from-aerosol generator for testing an emissions monitor, more particularly an airborne pollutant emissions monitor capable of detecting metal emissions. In addition, an embodiment can be employed as a simulator, e.g., simulating a large-scale boiler's exhaust stack. A third application is a standardized source of hazardous air pollutants provided as a dry aerosol, in particular metal-entrained dry aerosols.

BACKGROUND

The United States Environmental Protection Agency (EPA) recognizes 14 metals as air pollutants when emitted in exhaust emissions from sources such as the stacks of industrial incinerators, furnaces, and boilers. Conventionally, these sources are monitored for compliance with EPA regulations through a series of manual test methods. These methods require extraction of large volumes of exhaust gases from an exhaust stream over a period of one to three hours. The targeted emissions, e.g., metal aerosols, vapors, and particulates are collected in filters and typically are analyzed offsite. Recent technology now provides the capability to analyze emissions nearly continuously via robust in-stack sensors connected to onsite monitors. See U.S. Pat. No. 5,596,405, *Method and Apparatus for the Continuous Emissions Monitoring of Toxic Airborne Metals*, issued to Seltzer et al, Jan. 21, 1997. Historically, as the technology becomes available, EPA modifies regulations to take advantage of the improved capability. In this case, the regulations are re-written to include compliance criteria based on availability of "continuous emission" monitors that can readily provide emissions criteria over both short (e.g., one hour) and long (e.g., 24 hours) time intervals. Further, the new robust sensor/onsite monitor provides the inherent capability to time-resolve measurements and assure interim compliance in real time, heretofore unavailable using manual methods or low cost automated methods.

The majority of exhaust gas pollution emission analyzers use the detected species in the gaseous state. Among these are analyzers for detecting carbon monoxide (CO), nitrogen oxides ($NO_x$), and sulfur oxides ($SO_x$). Commercially prepared and certified gas mixtures are available as aerosols for use in evaluating emission analyzers. The same gas source can be introduced into the candidate analyzer and the reference analyzer, permitting a side-by-side comparison. Similarly, a specific gas mixture can be inserted into an exhaust gas stream to permit comparative measurements of in-stack sensors/monitors using both a candidate test method, e.g., a preferred embodiment of the present invention, and a reference test method, e.g., an EPA-approved manual method.

A significant factor in achieving EPA acceptance of the new generation of "in-stack" sensor/monitors is the ability to test them in the same "real time" that they are designed to operate. Further, the chosen test method should be efficient, accurate, and reliable for a wide range of exhaust streams and operational environments. Specific requirements include the ability to compare performance of the new monitoring technology to the EPA-approved reference methods for determining compliance, i.e., manually derived testing. One of the most basic problems to overcome in this comparison is providing representative exhaust streams composed of a known and relatively constant multi-element (metal) constituent for a given time period. Consider that the constituent need be both temporally consistent, i.e., be held constant, and offer a wide range of representative metals, including weight percentage levels, in the exhaust stream. That is, the concentrations of the various metals and the timeline for insertion in the exhaust stream should be known a priori and able to be controlled accurately over time.

Rarely does an unmodified exhaust stream exhibit metal emissions of the necessary elemental diversity and compositional and temporal stability to enable efficient, yet accurate and reliable, comparative testing. Metal emissions within a typical actual exhaust stream are sporadic, short-lived, and limited in elemental composition by the specific fuel or waste feed used as input. For example, inserting enough metal in the original fuel of a combustor (as metal oxides or salts, for example) to achieve emissions levels necessary to test the competing emissions sensors/monitors weld most likely violate the EPA's regulations for control of hazardous pollutants! Also, because the combustor is equipped with scrubbers and other emissions control devices to prevent excess emissions, providing enough excess metals at the input, i.e., in the fuel, may not be possible to attain the required levels for testing the sensors/monitors at the output, i.e., the exhaust stack.

Another method tried with little success is the insertion into the exhaust stream of metals via nebulization, i.e., spraying an aqueous metal solution. The theory is that given the high heat of the exhaust stream there will be sufficient latent heat to evaporate the water vapor in the nebulized metal solution, leaving a dry aerosol with entrained metals. However, experience with such methods has shown that in typical exhaust streams, the gases lack capacity to absorb additional moisture. This results in incomplete evaporation and water droplets containing entrained metals transit the exhaust stack. These droplets are deposited on the hardware used for manual extraction where they then quickly evaporate on the hot surface of the hardware and deposit metal for subsequent analysis. Thus, there is a dramatic difference between the results obtained with the candidate in-stack sensor/monitor and the EPA-approved manual method. The manual method can recover the evaporated metals on the hardware surface since the extraction hardware is washed and the metals recovered. No such provision is available for the "real time" in stack sensor/monitor.

Yet another approach is the generation and insertion of organic vapors with entrained metals. This is accomplished by chemically reacting two substances intentionally inserted and brought into close contact in the exhaust stream. A major disadvantage of this method is the toxicity of the substances needed to carry out the reaction. Further, even considering the handling difficulties of candidate substances, this method still does not provide the necessary aerosol needed to insure a valid test comparison. A viable solution need provide a source of:

- dry, multi-element aerosol with entrained metals of interest, dry aerosol-entrained metals independent of fuel or waste feed, and dry aerosol-entrained metals independent of temperature and moisture content, that ideally is compact, lightweight, easy to use, reliable, and provides a reproducible output.

Certified sources of metal air pollutants, similar to the commercially prepared gas mixtures noted above, are not presently available. Actual exhaust streams having entrained metals are primarily aerosols and particulates. Rarely do they consist of vapors. It is not practical, assuming physical possibility, to commercially prepare a homogenous mixture of targeted species (i.e., EPA-defined hazardous metals), contain it in a pressurized bottle, and be able to insert amounts of this mixture on a reproducible basis into a "front-end" of a sensor/monitor.

A solution to this testing problem is a system and method for introducing a dry gas mixture of known metal composition into the exhaust stream at known times and for known time intervals. It is not even critical at this juncture that the concentration of the gas/metal mixture be precisely known at input. So long as the mixture is inserted at a constant rate in the exhaust stream for consequent measurement using the manual EPA-approved method and the sensor/monitor to be tested, the system and method provide an efficient, reliable and accurate, solution. Insertion of the surrogate mix at or near the input end of the exhaust stream insures a homogenous mixture of existing exhaust gases and the surrogate mix by the time the exhaust stream reaches the sensor/monitor positioned near the output of the exhaust stream. Thus, a reliable alternate means for providing the necessary variety and levels of hazardous element emissions at the sensor/monitor, at a relatively constant level held relatively constant over a given time period, is provided as a preferred embodiment of the present invention.

SUMMARY OF THE INVENTION

A preferred embodiment of the present invention provides a method and apparatus for generating dry metal-containing aerosols, of known composition and concentration, and inserting same into an exhaust stream of a combustor. These dry aerosols simulate the entrained metal in hot exhaust gas that may be present in an exhaust stream from an industrial boiler, for example. They are inserted at a constant rate in order to support performance evaluation of multiple emission monitors as compared to a reference method such as EPA Method 29. Further, since the invention emits $CO_2$ and moisture, and these, elements are also present in the exhaust streams of actual combustors, an embodiment could serve as a "stand-alone" simulator to optimize design of emissions monitors and related systems associated with exhaust stacks.

A preferred embodiment of the present invention comprises:

a combustion chamber a fuel tank, a container for aqueous-entrained hazardous elements, e.g., metal salts a forced-air draft fan, a pump, a nebulizer, an air compressor, and metal ducting.

The combustion chamber may be of approximately 35–50,000 BTU capacity, although it is not limited to this range, but depends on the test setup. It can be fueled by kerosene, propane or other appropriate fuel, and be one of a number of commercially available small-scale industrial fan-forced heaters. The fuel tank may be integral with the apparatus encompassing the combustor. The forced-air draft fan also may be integral with the apparatus encompassing the combustor and is capable of providing approximately 100–200 $ft^3$/min to the combustion chamber. The fan is also of sufficient capacity to overcome effects of static pressure and fluctuations resulting from contact of the inserted mixture with the hot gases of the exhaust stream.

The pump can be a peristaltic or other type of pump able to provide the aqueous stream from the container of metal salts to the nebulizer at a fixed constant rate. The nebulizer, powered by the air compressor, is capable of generating a fine liquid aerosol from the aqueous stream provided from the container. The metal ducting connects the output of the nebulizer to the exhaust stack confining the exhaust stream.

As the fine aerosol stream is inserted into the hot combustion chamber, some of the metal salts are thermally decomposed, resulting in combustion and subsequent oxidation of the metal constituents. The metal salt and metal oxide aerosols are then entrained in the fan-forced draft, transit the ductwork, and enter the exhaust stream as a dry aerosol. The fan-forced draft is adjustable to insure proper aspiration and optimal pressure in the combustion chamber of the heater.

To ensure test reproducibility, an aqueous solution of metal salts of known composition and concentration is made available. A peristaltic pump incorporating a variable and controllable rate, withdraws the metal-entrained liquid from its container and delivers it to a nebulizer at a constant rate. Given a priori knowledge of the solution makeup, i.e., number of mg/l of each metal in solution, and the pump's delivery rate, i.e., 1/min, then the rate and composition of metals inserted into the exhaust stream can be determined.

Also knowing a priori the exhaust stream flow rate, and assuming that 100% of the metal-entrained aerosol is inserted, entrained in the exhaust stream, and homogeneously mixed prior to receipt at the sensor/monitor, an exhaust gas metal concentration can be approximated. This provides a theoretical maximum concentration, or upper bound, on the metal concentration to be expected at the sensor/monitor. It also provides equal amounts of a dry gas, homogeneously mixed in the exhaust stream, to the candidate sensor/monitor and the hardware inserted for manually taking data using EPA-approved methods for comparison and performance evaluation.

The hardware setup and attendant method of a preferred embodiment of the present invention is applicable to any metal that exists as a water-soluble salt, and to any element, inorganic or organic, that one wishes to investigate, not just the 14 metals currently on the EPA list of hazardous metal air pollutants.

In another preferred embodiment of the present invention, an incinerator simulator is envisioned. Since the combustion chamber generates by-products of combustion, e.g., $CO_2$ and $H_2O$, that closely simulates that of an industrial boiler, for example, it may be used as a simulator of the boiler. Thus, a preferred embodiment of the present invention can be set up for use in factory or customer testing of emissions monitors prior to installation in large stacks. It can also be used for research and development where optimization of design is the goal. For example, dilution of combustor exhaust using ambient air reduces exhaust gas temperatures to values approximating actual exhaust streams of large-scale industrial combustors. The combustor is configured in much the same way as above except that it is connected to a "mini-stack" for simulation of an actual large-scale exhaust stack. Note that regulatory permits may be required for operation of the simulator since it will be exhausted to the atmosphere in the typical test.

A third embodiment of the present invention is as a standard source for surrogate metal-entrained atmospheric emissions. The benefit of using this embodiment for such a source is the precise control of all parameters that is possible using such an embodiment. For example, in a typical application strict control of the aqueous metal solution inserted into an entraining airflow is possible for establishing the required accurate reproducibility. Also, this application requires an embodiment of the present invention to undergo rigorous validation tests and certification procedures and since it uses essentially commercial off-the-shelf (COTS) components, the certification also should be straightforward. At present, there are no standardized sources of metal-entrained aerosols, thus this embodiment has high value to the environmental community for direct testing of emissions monitoring systems and methods.

Advantages of preferred embodiments of the present invention, as compared to conventional systems, include permitting:

simplified test systems using COTS hardware;

use of reconfigurable pumps;

simplified design of alternate configurations;

inexpensive fabrication;

reduced man-hours for operation;

reduced system complexity;

reduced system capital costs;

improved test robustness;

low maintenance costs;

increased flexibility in test conduct;

fewer tests or higher duty factor per test or both;

high reliability; and ready upgradability.

Embodiments of the present invention can be applied to testing and optimization of hazardous air pollutant emissions monitors of all method types including: plasma emission-based, laser-based, electric spark, X-ray fluorescence, and manual methods involving, for example, filter capture of metal aerosols for later analysis. This saves capital equipment, as well as training and maintenance, costs. Further, a preferred embodiment of the present invention may be used in simulators or standardized sources that will cost less and provide more accurate and easily interpreted data for training and updating operators and maintenance technicians.

Preferred embodiments are fully disclosed below, albeit without placing limitations thereon.

DETAILED DESCRIPTION

Figure 1:
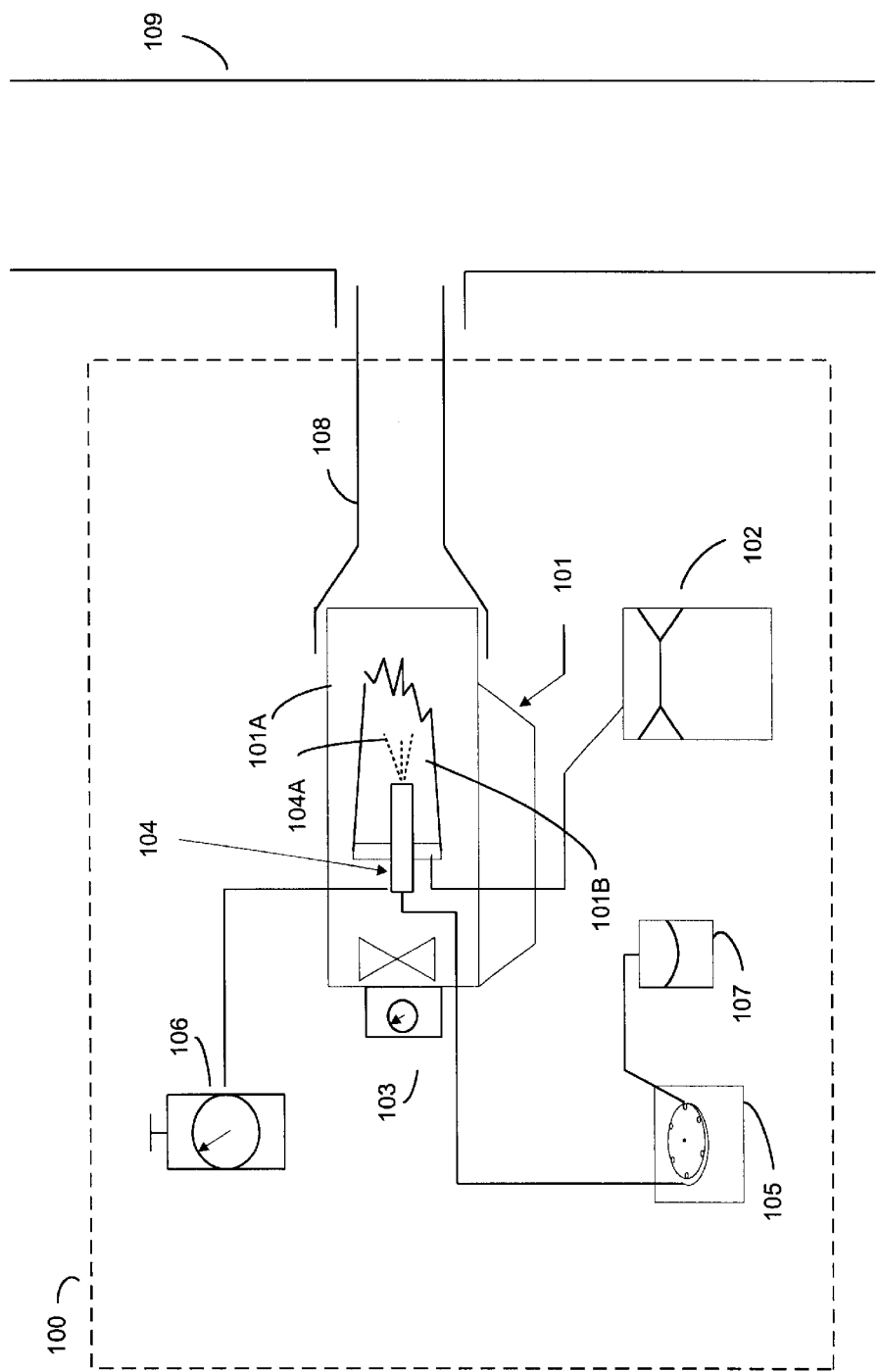
FIG. 1 depicts relative positions of components in a preferred embodiment of the present invention as installed proximate an actual exhaust stack.

A preferred embodiment of the present invention, the apparatus 100 of FIG. 1, incorporates:

a fan-forced heater 101 sized from 35–50,000 BTU;

a fuel source 102 such as a propane tank;

a forced-air draft fan 103 that may be integral to the heater 101;

a nebulizer 104 that consists essentially of a tube for intaking a fluid and compressed air and outputting a fine spray, i.e., a "wet" aerosol;

a pump 105 such-as a peristaltic pump, for providing a constant rate of fluid to the nebulizer 104;

a regulated source of compressed aid 106, such as a regulated air compressor;

a container of metal-entrained aqueous solution(s) 107 of known concentration and composition; and ductwork 108 connecting the output of the combustion chamber 101A of the heater 101 to an exhaust stack 109.

The-combustion chamber 101A of a small-scale industrial fan-forced propane or kerosene heater 101 suffices for heating the fine spray 104A of the nebulizer 104, thus drying it sufficiently to mix homogeneously as a "dry" aerosol when inserted into the exhaust stack 109. The draft fan nominally provides an airflow of 100–200 ft$^3$/min to overcome the effects of static pressure and pressure fluctuations arising from contact with the hot stack gases.

The COTS heater 101 is modified as follows to optimize operation of this embodiment of the present invention:

a. A pneumatic nebulizer 104 such as concentric glass nebulizer or V-groove type, is mounted behind e rear partition (not separately shown) of the combustion chamber 101A. The nebulizer's outlet orifice (not separately shown) is oriented such that a conical spray pattern 104A is directed through a hole in the partition at the rear of the combustion chamber 101A toward the flame zone 101B of the combustion chamber 101A so that maximum interaction between the spray and the flame is achieved. Temperatures within the chamber 101A typically exceed 500° C. This provides sufficient latent heat to completely evaporate the moisture within the spray 104A, yielding a dry aerosol (not separately shown) having entrained metals of the initial solution. A glass nebulizer 104 must be recessed sufficiently to avoid damage from the flame.

b. At the high temperatures of the combustion chamber 101A, some of the metal salts thermally decompose, combust, and oxidize the metal constituent. The remaining metal salts, together with the oxidized metal, are entrained in the fan-force draft air and inserted via the ductwork 108 into the stack 109.

c. The forced-air fan is provided with a means to adjust the flow of forced air to the combustion chamber, such as a rheostat (not separately shown) for controlling fan speed or a movable baffle (not separately shown) in the input air duct to manually reduce air flow as needed.

To ensure that the surrogate metal-entrained gases are generated at a constant rate that is reproducible, a container 107 of a solution, such as an aqueous solution, of dissolved metals of known composition and concentration is provided. A peristaltic pump 105, incorporating a speed control, withdraws fluid from the container 107 and delivers it to the nebulizer 104 at a given constant rate.

Note that if the concentration of the individual metal(s) in the solution(s) in mg/l and the pump's delivery rate in 1/min are known, then the rate of insertion of the surrogate into the stack 109 can be readily determined. For example, a solution containing 1000 mg/l of Chromium (Cr) introduced to the nebulizer 104 at 0.010 l/min, provides a surrogate sample of Cr at 10 mg/min (10,000 μg/min) to the stack 109. Assuming that the exhaust stream flow rate is known and that 100% of the metal-entrained aerosols are inserted into the stack 109, entrained in the hot exhaust stream, and homogeneously mixed therein, an approximation of the metal content of the exhaust gas can be made. For example, if our Cr sample above were introduced into an exhaust stream flow of 100 $m^3$/min, a concentration of 100 $\mu g/m^3$ is expected to be the upper bound Cr concentration within the exhaust stream, assuming that the original (unsupplemented) exhaust stream contained negligible Cr.

Also, note that this method is not intended to provide exhaust stream concentrations of an exact value since insufficient data exist on the actual transport mechanism of the surrogate aerosol as it mixes in the exhaust stream. Rather, the above process provides an upper bound, a theoretical maximum concentration. The reference test hardware and EPA-approved manual data analysis method can provide a near approximation of the actual emissions that the candidate emissions sensor/monitor is to quantify.

The above described example method is applicable to any salt dissolvable in water. In the case of mercury (Hg), for, example, insertion of aqueous aerosols of mercuric nitrate ($HgNO_3$) or other Hg salt, into the combustion chamber 101A results in the generation of a large fraction of Hg vapor, since Hg salts have a low decomposition temperature and Hg metal has a low boiling point. It is possible that other metals will vaporize similarly but oxidize downstream upon a reduction in gas temperature within the stack 109 relative to the temperature in the combustion chamber 101A.

An additional advantage of the "real time" evaluation of emissions sensor/monitors afforded by a preferred embodiment of the present invention involves determining the response time of the sensor/monitor. By abruptly terminating the introduction of the surrogate solution to the burner, the amount of time required for the emissions sensor/monitor to recognize the reduction in emissions can be measured. A typical standard for response time is the time it takes for the sensor/monitor to recognize a falloff of 90% in emission level when a step change to zero in surrogate introduction is effected. Using a preferred embodiment of the present invention, this procedure can be conducted and evaluated during actual testing.

Figure 2:
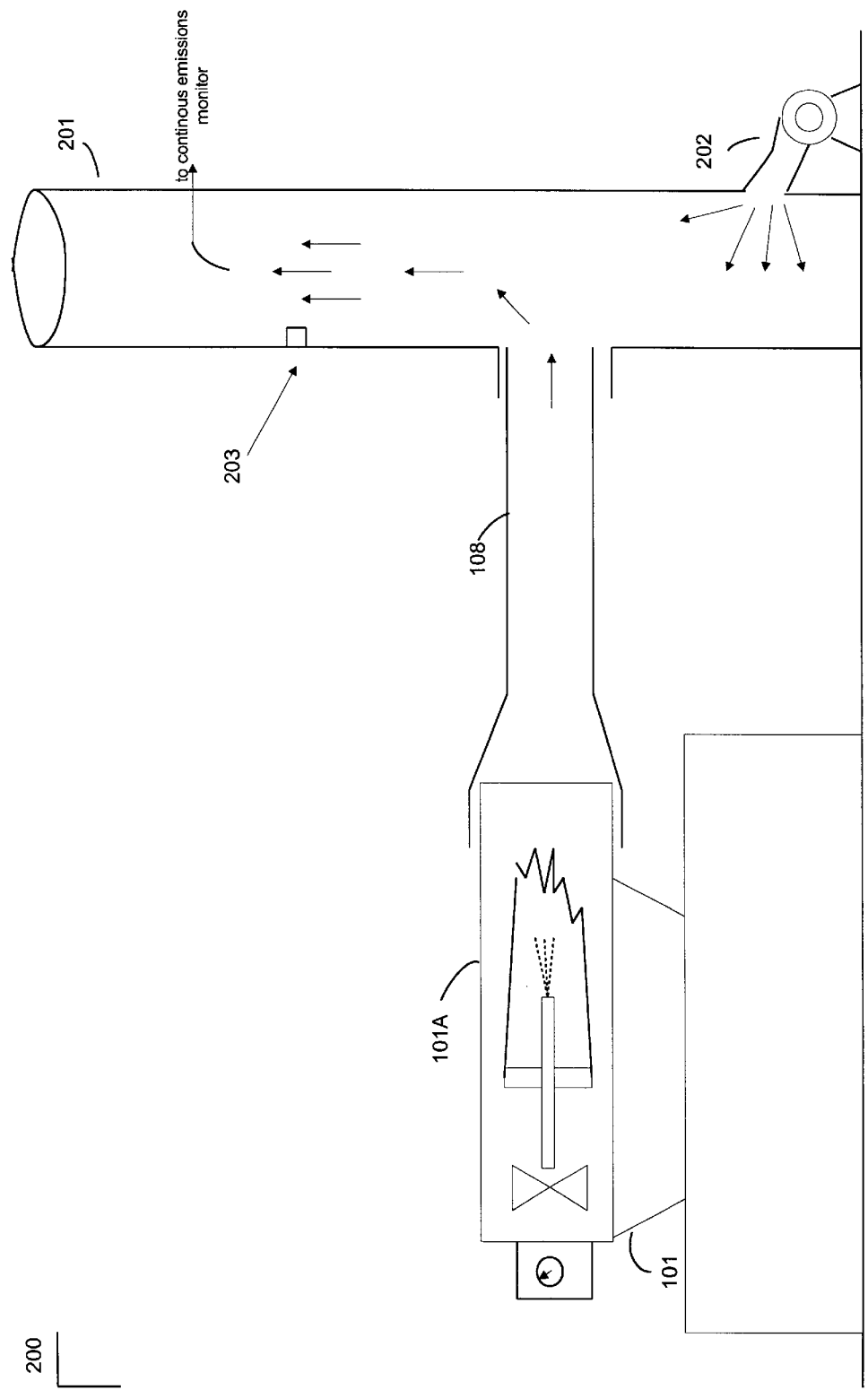
FIG. 2 represents a preferred embodiment of the present invention used as a simulator.

In another preferred embodiment of the present invention, an apparatus very similar to the above described is used as a portable simulator of a large-scale exhaust stack such as may be used with an industrial boiler. Referring to FIG. 2, the same burner arrangement is used, however, FIG. 2 shows only the heater 101 and ductwork 108 for simplicity. Since the heater 101 generates byproducts similar to a large industrial boiler, for example, $CO_2$ and $H_2O$ as vapor, it is feasible to deploy a portable apparatus such as described above for research and development or on-site testing of emissions sensors/monitors at a manufacturer's facility. There would be no need to seek out an actual large scale combustor to conduct these basic tests and design investigations. Dilution of the heater's exhaust using ambient air would provide a surrogate exhaust stream closely resembling that of an actual industrial combustor.

Specifically, the configuration of FIG. 1 may be assembled as follows:

a. the propane (or kerosene) fan-forced heater 101 is connected to a fuel tank 102, such as a pressurized liquid propane tank. A COTS heater 101 is most desirable since provisions exist for fuel connection, storage, delivery, and regulation.

b. the heater 101 is connected via ductwork 108 to an inlet port (not separately shown) of the exhaust stack 109. The ductwork 108 is of sufficient diameter to eliminate excess backpressure on the heater 101 from the hot exhaust stream. A minimum inside diameter of 4 inches for ductwork 108 no longer than 4 feet is optimum for connecting the end of the conical ductwork 108 to the port of the stack 109. The ductwork 108 is flexible metal curved upward from the heater 101 to facilitate aspiration and entrainment of the inserted hazardous element, e.g., EPA-hazardous metals, aerosols, while minimizing static pressure on the heater 101.

c. a source of regulated compressed air 106, such as a regulated air compressor, is connected to the nebulizer 104 and adjusted to approximately 30 psi.

d. the inlet of the regulated pump 105, such as a peristaltic pump, is attached to a length of plastic tubing (not separately shown) and the other end of the plastic tubing is attached to an outlet of the container of metal salt solution(s) 107.

e. the outlet of the pump 105 is attached to the inlet of the nebulizer 104 using a second length of plastic tubing (not separately shown).

f. the heater 101 is ignited and the flame allowed to stabilize.

g. the pump 105 is started, providing a constant flow of aqueous metal solution to the nebulizer 104 and simultaneously the air compressor 106 is started, providing necessary pressure to generate a fine spray ("wet aerosol") 101A from the solution inserted by the pump 105 at the input of the nebulizer 104 prior to output from the nebulizer 104 to the combustion chamber 101A.

h. the spray of the nebulizer 104A is directed into the flame zone 101B of the combustion chamber 101A where the water component is evaporated, yielding a dry metal salt entrained in an aerosol. Depending on the thermal and chemical characteristics of the metal salt, it may thermally decompose, resulting in atomization of the metal constituent. Thus, the atomized metal will oxidize in the flame 101B and exit the combustion chamber 101A as a solid particle. The metal salts that resist decomposition will exit as a "dry" metal-entraining aerosol. For highly volatile metals, such as Hg, the metal may exit the combustion chamber 101A as a metallic vapor.

i. varying the chemical composition of the aqueous solution, e.g., nitrates, chlorides, phosphates, etc., it is possible to affect the chemical form of the combustion product exiting the combustion chamber 101A.

j. multi-element solutions are possible so long as the individual constituents are chemically compatible in solution. For example, cobalt chloride ($CoCl_2$) and silver nitrate ($AgNO_3$) are incompatible, causing the precipitation of the insoluble precipitate silver chloride (AgCl). Thus, to accommodate metal compounds that are otherwise incompatible in a single aqueous solution, multiple solutions can be prepared and stored in separate containers with multiple lines to multiple pumps or a multi-channel pump 105 and a separate dedicated nebulizer 104 for each solution, given that "time multiplexing" is not desired.

In FIG. 2, the entire apparatus is partially represented as the modified heater 101 and ductwork, 108 and it is understood that the missing components of FIG. 1 are also a part of this configuration but omitted from FIG. 2 for simplicity.

The heater 101 heats the surrogate mixture and inserts it into the ductwork 108 in the same fashion as for the first embodiment above. However, the stack into which the surrogate is inserted is a "mini-stack" 201. This mini-stack 201 has no intrinsic flow of "real" exhaust gases. Rather, it is a simulation of an actual stack, and actual stack gases are simulated by the provision of ambient air via a variable speed draft blower 202 at the bottom of the mini-stack. The speed of the blower 202 can be varied electronically, or operated at maximum speed and airflow controlled via flow dampers in the ducting. By adjusting the flow of ambient air, the concentration of $CO_2$, $H_2O$, and surrogate metals can be varied to meet test requirements. Since the exhaust from this "simulator" must be vented to atmosphere, an operating permit may have to be obtained from state and local regulators. A sampling probe 203, representing the in-stack sensor is placed near the mini-stack's exit to simulate the position of a candidate emission's sensor. The output of the sensor is then sent to an appropriate monitor (not separately shown) for display and subsequent evaluation.

Figure 3:
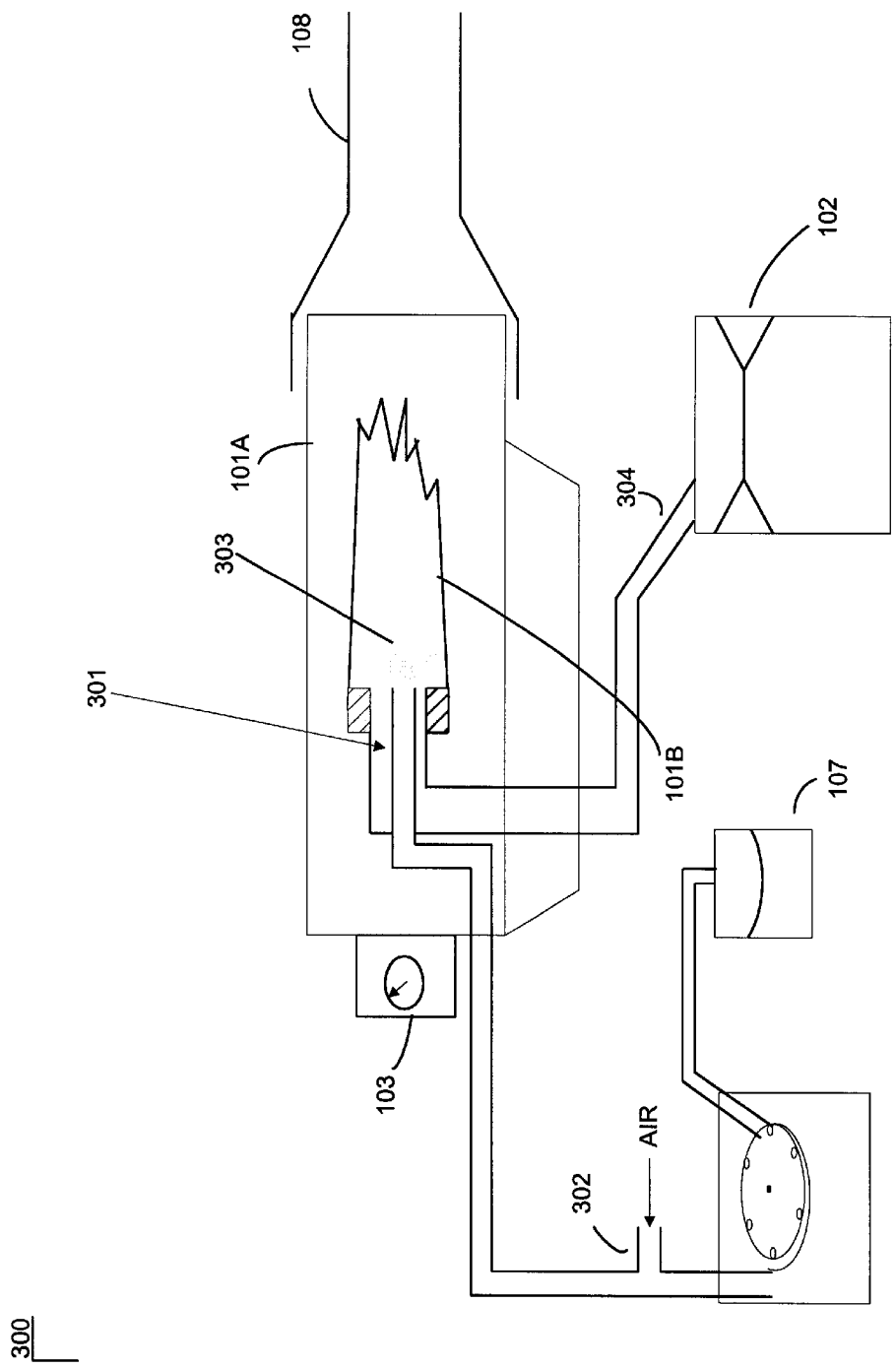
FIG. 3 represents an alternative configuration to the nebulizer depicted in FIG. 1.

Referring to FIG. 3, an alternate burner configuration 300 is depicted. The burner (not separately shown) is termed a "total consumption burner." The total consumption burner eliminates the need for a nebulizer 104 by providing a feed path 301 for the surrogate solution from the source 107 through an orifice (not separately shown) directly to the combustion zone 101B of the burner. A preferred fuel for the total consumption burner is hydrogen gas mixed with oxygen gas or air. This feed path 301 is provided concentric with and through the fuel feed path 304. Note that the stream 303 provided to the combustion zone 101B is still a fluid aerosol spray. An air intake 302 is provided to help draw the surrogate solution directly from the source 107 by the pressure difference between the pressure within the combustion chamber and ambient air. The inherent value of this configuration is that there is some assurance that 100% of the surrogate solution is getting to the combustion zone, thus 100% of the dissolved surrogate will interact with the flame. In this way, an investigator is able to quantify the amount of surrogate fed to the combustion zone. The nebulized aerosol spray could possibly divert some of the surrogate to the side of the combustion chamber and not react all of the surrogate with the flame.

A third application for a preferred embodiment of the present invention is that of a standardized source of metal-entrained aerosols. This application may well be suited to the use of the total consumption burner as described above. A standardized source requires precise control of operating parameters. Since the material and components used in the above described embodiment of the present invention can be COTS hardware, including the total consumption burner, and the process for implementing the method of the present invention is straightforward, the precise control needed for a "standard" source is achievable. For example, strict control of aqueous metal introduction and air flow are two primary requirements that have been detailed above in relation to the peristaltic pump, the regulated air compressor, and even the blower used on the simulator version.

The above descriptions should not be construed as limiting the scope of the invention but as mere illustrations of preferred embodiments. For example, although examples discussed hazardous metal constituents at length, the method and apparatus is applicable to any surrogate, hazardous or not, organic or inorganic, that a user may need to introduce into an exhaust stream. The scope shall be determined by appended claims as interpreted in light of the above specification.

We claim:

1. An apparatus for inserting a compositionally consistent and diverse surrogate in solution from a source, at a given rate, into an exhaust stream confined in a structure, comprising:

a regulated pump, having an input and an output, said input operably connected to the surrogate source;

a burner;

a combustion chamber having a combustion zone, said chamber having an input and an output, operably connected to said burner;

a fuel source operably connected to said burner;

a source of forced air, capable of regulation, operably interfaced to said combustion chamber;

an air source, capable of regulation, having an input and an output;

a device for inputting the surrogate in solution to said combustion chamber, said device having an input and an output, and operably connected at said device's input to said pump's output and to said air source's output; and a connection from said combustion chamber's output to the structure,
wherein said surrogate in solution is combusted by said burner in said combustion chamber, and
wherein said output of said combustion chamber is input to the structure via said connection, and
wherein the surrogate is presented continuously to an emissions sensor.

2. The apparatus of claim 1 wherein said fuel source is a container for holding a fuel, said pump is a peristaltic pump, said air source is a regulated air compressor, and said source of forced air is a variable-speed fan.

3. The apparatus of claim 1 wherein said device is a nebulizer that converts said surrogate in solution to a fine spray and directs said fine spray into said combustion chamber.

4. The apparatus of claim 1 wherein said burner is a total consumption burner and said air source may be ambient air, and
wherein said surrogate in solution is aspirated directly into said combustion zone of said combustor chamber through an orifice, and
wherein a quantitative transfer of the surrogate in solution is enabled.

5. The apparatus of claim 1 wherein said burner is fired by a fuel selected from the group consisting of: kerosene, propane, butane, compressed natural gas (CNG), and natural gas.

6. The apparatus of claim 5 wherein said fuel is kerosene.

7. The apparatus of claim 4 wherein said total consumption burner is fired by hydrogen gas.

8. The apparatus of claim 1 wherein ductwork, having a largest inside dimension tapering from said combustion chamber output to less than about 4.5 inches at the structure and a length less than about four feet six inches, is part of said connection.

9. The apparatus of claim 1 wherein said apparatus is portable.

10. The apparatus of claim 1 wherein said apparatus is essentially a metal-entraining aerosol generator.

11. The apparatus of claim 1 wherein said apparatus provides a standardized source of metal-entraining aerosols.

12. A method for inserting a compositionally consistent and diverse surrogate from a source, at a given rate, into an exhaust stream confined in a structure for the purpose of evaluating a sensor, comprising:

providing a fluid containing the-surrogate to a combustion chamber;

heating said fluid so that it evaporates essentially all liquid content, yielding an essentially dry mixture; and inserting said resulting dry mixture into the exhaust stream, wherein said dry mixture may comprise an aerosol, a solid, and a vapor, and wherein said dry mixture mixes homogeneously in the exhaust stream, and wherein the surrogate is presented to an emissions monitor.

13. An apparatus for simulating emissions, said apparatus interfacing a surrogate source, comprising:

a regulated pump, having an input and an output, said input operably connected to the surrogate source;

a burner;

a combustion chamber, having an input and an output, operably connected to said burner;

a fuel source operably connected to said burner;

a first source of forced air, capable of regulation, operably interfaced to said combustion chamber;

an air source, capable of regulation, having an input and an output;

a device for inputting the surrogate in solution to said combustion chamber, said device having an input, and an output, and operably connected at said device's input to said pump's output and to said air source's output;

a second source of forced air, capable of being varied, operably connected to at least one said input of said structure; and a connection from said combustion chamber's output to the structure, wherein said surrogate in solution is heated by said burner in said combustion chamber, and wherein said output of said combustion chamber is input to the structure via said connection, and wherein a flow of air is established within said structure by said second source, and wherein said output of said combustion chamber is mixed with said flow of air to simulate an exhaust stream of a large-scale combustor.

14. The apparatus of claim 13 wherein said device is a nebulizer that converts said surrogate in solution to a fine spray and directs said fine spray into said combustion chamber.

15. The apparatus of claim 13 wherein said burner is a total consumption burner and said air source may be ambient air, and wherein said surrogate in solution is aspirated directly into said combustion zone of said combustor chamber through an orifice, and wherein a quantitative transfer of the surrogate in solution is enabled.

16. The apparatus of claim 13 wherein said fuel source is a container for holding a fuel, said pump is a peristaltic pump, said source of pressurized air is a regulated air compressor, said first source of forced air is a forced-air fan, the output of said forced-air fan being variable, and said second source of forced air is a blower having speed control or adjustably restrictive ductwork operably connecting with said structure, or both.

17. The apparatus of claim 13 wherein said burner is fired by a fuel selected from the group consisting of: kerosene, propane, butane, compressed natural gas (CNG), and natural gas.

18. The apparatus of claim 17 wherein said burner is fired by kerosene.

19. The apparatus of claim 17 wherein said burner is fired by propane.

20. The apparatus of claim 13 wherein ductwork, having a largest inside dimension tapering from said combustion chamber output to less than about 4.5 inches at the structure and a length less than about four feet six inches, is part of said connection.

21. The apparatus of claim 13 wherein said structure is a scaled-down exhaust stack.

22. The apparatus of claim 13 wherein said apparatus is portable.

23. The apparatus of claim 13 wherein said apparatus provides an exhaust stream simulator.

24. A method for simulating an exhaust stream containing a surrogate-entraining gas in a scaled-down stack, comprising:

introducing air into the scaled-down stack to create an upward airflow;

providing a fluid containing the surrogate to a combustion chamber;

heating said fluid so that it evaporates essentially all liquid content, yielding an essentially dry mixture; and inserting said resulting dry mixture into the simulated exhaust stream;

wherein said dry mixture may comprise an aerosol, a solid, and a vapor, and wherein said dry mixture mixes essentially homogeneously in the exhaust stream, and wherein said introduced air is used to control simulation conditions.

* * * * *